United States Patent [19]

Joyce, Jr. et al.

[11] Patent Number: 5,186,860
[45] Date of Patent: Feb. 16, 1993

[54] INERT ELECTRODE COMPRISING A CONDUCTIVE COATING POLYMER BLEND FORMED OF POLYANISIDINE AND POLYACRYLONITRILE

[75] Inventors: James L. Joyce, Jr.; Warren C. Jones, both of Winston-Salem; David F. MacInnes, Jr., Greensboro, all of N.C.

[73] Assignee: AMP Incorporated, Harrisburg, Pa.

[21] Appl. No.: 596,066

[22] Filed: Oct. 11, 1990

Related U.S. Application Data

[63] Continuation-in-part of Ser. No. 527,799, May 23, 1990, abandoned.

[51] Int. Cl.$^5$ .............................................. H01B 1/00
[52] U.S. Cl. .................................. 252/500; 252/512; 252/518; 428/411.1
[58] Field of Search ................. 252/500, 518; 428/411

[56] References Cited

U.S. PATENT DOCUMENTS

| H944 | 8/1991 | Wade, Jr. et al. | 252/500 |
|---|---|---|---|
| 4,803,096 | 2/1989 | Kuhn et al. | 252/500 |
| 4,851,487 | 7/1989 | Yaniger et al. | 252/500 |
| 4,869,949 | 9/1989 | Muenstedt | 428/216 |
| 4,935,164 | 6/1990 | Wessling et al. | 252/500 |
| 4,940,517 | 7/1990 | Wei | 204/78 |

FOREIGN PATENT DOCUMENTS 0352882  1/1990  European Pat. Off. .

OTHER PUBLICATIONS

Travers et al.; Polyaniline: A Material Still Under Discussion; Synthetic Metals, 35 (1990) pp. 159-168.
Dao et al.; Design and Optical Modulation of Electrochromic Windows; IECEC-89; Aug. 6-11, 1989; pp. 1736-1741.
Gregory et al.; Conductive Textiles; Synthetic Metals, 28 (1989) pp. C823-C835.
MacDiarmid et al.; "Polyaniline": Interconversion of Metallic and Insulating Forms; Mol. Cryst. Liq. Cryst. 1985, vol. 121, pp. 173-180.
Chevalier et al.; Poly(N-benzylaniline): a soluble electrochromic conducting polymer; Polym. Commun. vol. 30, No. 10, 1989, pp. 308-310.
Nguyen et al.; Poly(N-Benzylaniline)/(Poly(AMPS)-/WO$_3$ Solid State Electrochromic Cell; Jrnl. of the Electrochem. Soc. Jul. 1989; pp. 2131-2132.
Shimidzu; Derivatization of Conducting Polymers with Functional Molecules Directed via Molecular Structural Control Towards a Molecular Device; Reactive Polymers, 11 (1989) pp. 177-189.
Wang et al.; Conducting Polymer Blends: Polythiophene and Polypyrrole Blends with Polystyrene and Poly(bisphenol A carbonate); Macromolecules, vol. 23, No. 4, 1990; pp. 1053-1059.

(List continued on next page.)

Primary Examiner—Paul Lieberman
Assistant Examiner—Bradley A. Swope

[57] ABSTRACT

The compound ortho-methoxyaniline (o-anisidine) can be polymerized by both chemical and electrochemical means to produce polyanisidine, a soluble polymer of high electrical conductivity. Also called poly-o-methoxyaniline or PANIS, polyanisidine can be further blended with various other polymers enabling construction of devices with desirable electrical, optical and physical properties. Oxidative polymerization yields have been increased to 47 percent with no apparent loss in electrical conductivity. PANIS has been blended with polystyrene, polyacrylonitrile, polyethylene oxide and poly(trimethyl hexamethylene terephthalamide) (nylon) to form free-standing, stable, flexible films and fibers having electrical resistance values dependent upon the concentration of PANIS. The applicability of PANIS technology has been demonstrated with the construction of three devices: a switching device that will change color upon the application of positive and negative voltages, an inert polymer electrode, and an electromagnetically shielded connector.

7 Claims, 6 Drawing Sheets

OTHER PUBLICATIONS

Zinger et al.; Electrocoating of carbon fibres with polyaniline and poly (hydroxyalkyl methacrylates); Polymer, 1989, vol. 30, Apr. pp. 628–635.

Gottesfeld et al.; On the Mechanism of Electrochemical Switching in Films of Polyaniline; J. Electrochem. Soc. 1987, vol. 134, No. 1; pp. 271–272.

MacDiarmid et al.; The Polyanilines: Processing, Molecular Weight, Oxidation State and Derivatives; Polym. Prepr. (Am. Chem. Soc., Div. Polym. Chem.) 1989, vol. 30, No. 1, pp. 147–148.

Huang et al.; Polyaniline, a Novel Conducting Polymer; J. Chem. Soc., Faraday Trans. 1, 1986, 82, 2385–2400.

Laakso, et al; Conducting Polymer Blends; Synthetic Metals, 28(1989) C467–C471.

Kaner et al.; Plastics That Conduct Electricity; Scientific American; Feb. 1988; pp. 106–111.

Macinnes et al.; Poly-o-Methoxyaniline: A New Soluble Conducting Polymer; *Synthetic Metals,* 25 (1988) 233–242.

Batich et al.; Chromatic Changes in Polyaniline Films; J. Electrochem. Soc. vol. 137, No. 3, Mar. 1990, pp. 883–885.

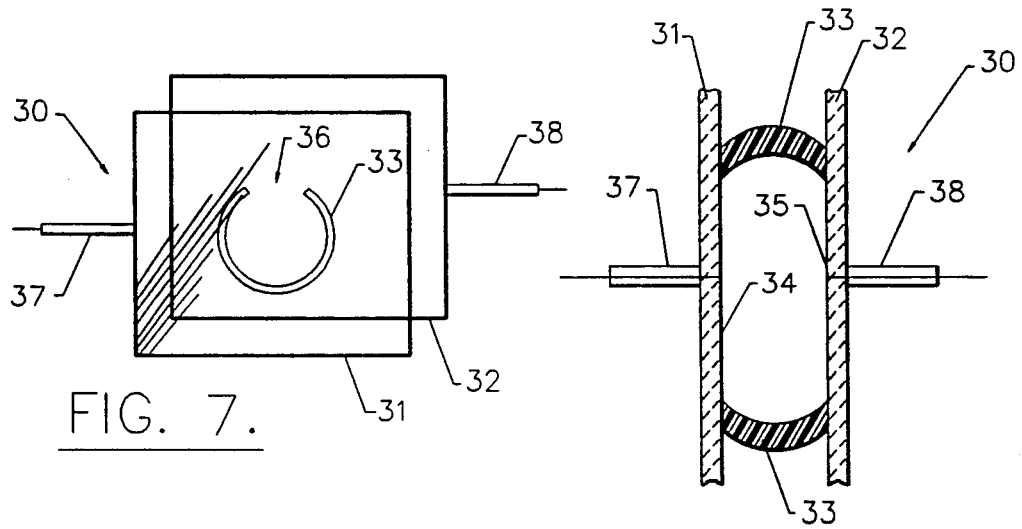
FIG. 7.
FIG. 8.
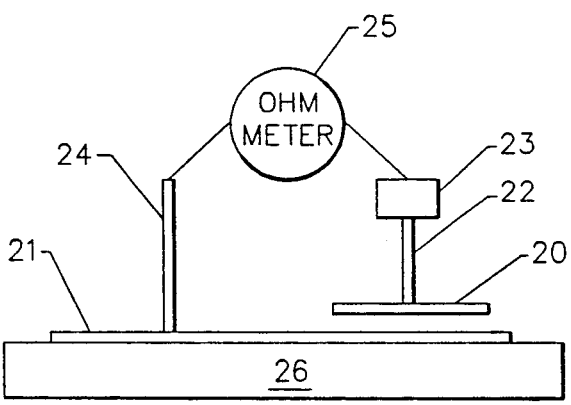
FIG. 9.
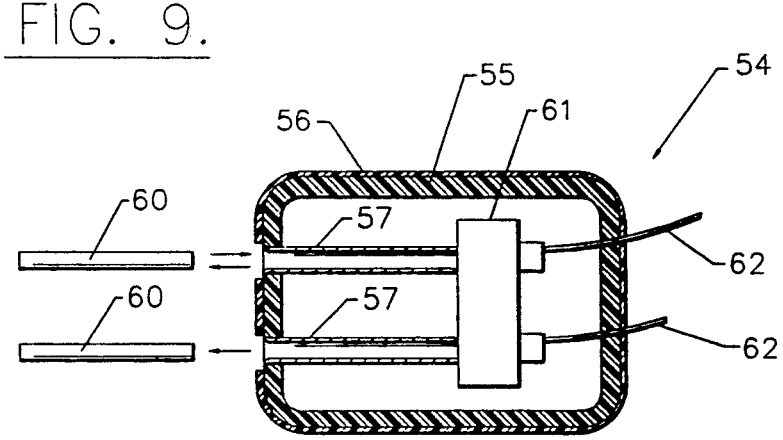
FIG. 10.

INERT ELECTRODE COMPRISING A CONDUCTIVE COATING POLYMER BLEND FORMED OF POLYANISIDINE AND POLYACRYLONITRILE

FIELD OF THE INVENTION

The present invention relates to conductive polymers, and in particular relates to an intrinsically conductive polymer of ortho-methoxyaniline (also called o-anisidine), hereinafter referred to as polyanisidine or PANIS, blends of PANIS with other polymers for forming such blends, and the resulting products. This application is a continuation in part of application Ser. No. 07/527,799, filed May 23, 1990, inventors Jones, Joyce, and MacInnes for "Conductive Polymer Blends."

BACKGROUND OF THE INVENTION

Electrically conductive polymers are of increasing interest for a number of applications, particularly those where electrical conductivity is desired or required and where the physical property of an organic polymer would likewise be advantageous.

One technique for producing electrically conductive polymers has been the bulk mixture of conductive particles such as carbon black in a polymer until the population of the conductive particles is sufficient to carry a desired amount of current in spite of the insulating property of the polymer carrying the conductive material.

As used herein, however, the term "electrically conductive polymer" refers to organic polymers that can be made intrinsically conductive without the addition of metal or other conductive fillers. Such polymers offer the properties of electrical conductivity along with the properties and advantages of polymers to thereby produce relatively versatile materials advantageous in a number of applications.

Certain intrinsically electrically conductive polymers are given their electrical conducting properties through a process known as "doping." In general, doping is a process by which the polymer is treated with an oxidizing or reducing agent for a sufficient period of time to give a partially oxidized or partially reduced material that is electrically conductive.

As used herein, the term "electrically conductive" means that the conductivity of the material as measured in ohm$^{-1}$ cm$^{-1}$ or Siemens/cm exceeds $1 \times 10^{-7}$.

Although conductive polymers have been generally known for some time, practical applications of them have been limited because those known generally tend to be brittle, lack flexibility, abrade easily, are insoluble in their conducting states, and tend to decompose upon heating before they soften.

Therefore, one potential solution to these problems has been to attempt to blend conductive polymers with other polymers having desirable physical properties to get a resulting blend which maintains its conductive properties, but which also exhibits better physical properties. To date, however, it has been generally difficult to obtain such mixtures because the available conductive polymers were not soluble in their conducting state. As known to those familiar with conductive polymers, the resulting processes require that the conductive polymers be chemically changed to a non-conducting state, disolved, mixed with other polymers, removed from the solvent, and then redoped to change the potentially conductive polymer back into a conducting state. In turn, carrying out the doping process in a mixed polymer matrix can become complicated.

Recently, however, some progress has been reached in this particular field. In U.S. patent application No. 07/203,688, inventors MacInnes and Funt, filed June 9, 1988 for "Soluble Conducting Polymers of Poly-O-Methoxyaniline", there is disclosed an electrically conductive polymer of orthomethoxyaniline that is also referred to as "polyanisidine." Polyanisidine has the unusual advantage of being soluble in a number of relatively common organic solvents in which other polymeric materials are similarly soluble. The contents of Ser. No. 07/203,688, now abandoned, are incorporated entirely herein by reference.

As a follow-up to the U.S. patent application No. 07/203,688, now abandoned, recent progress has further been made in blending polyanisidine with other polymers, often referred to as "engineering" polymers which offer the chemical and physical properties for which polymeric materials are often desired.

Work has progressed with respect to polyanisidine and its blends, however, and there remains the need for identification and development of improved synthesis of the blends and appropriate technological applications that take full advantage of polyanisidine and its properties.

Object of the Invention

Therefore, it is an object of the present invention to produce conductive polymer blends that exhibit improved physical and electrical properties, to improve the processes for making such polymer blends, and to develop applications for the polymer blends, including chemically inert electrodes and electromagnetic shielding devices. It is also an object of the invention to produce electro-optical devices that take advantage of the physical color changes to which certain conductive polymers exhibit when subjected to an electric potential.

The foregoing and other objects, advantages and features of the invention, and the manner in which the same are accomplished, will become more readily apparent upon consideration of the following detailed description of the invention taken in conjunction with the accompanying drawings, which illustrate preferred and exemplary embodiments, and wherein:

FIG. 7 is a partial perspective view of an electrooptical device incorporating an intrinsically electrically conductive polymer of the present invention;

FIG. 8 is a cross sectional view of an electrooptical cell incorporating an intrinsically electrically conductive polymer of the present invention;

FIG. 9 is a schematic view of the apparatus used to measure the conductivity of various polymers and polymer blends; and FIG. 10 is a cross sectional view of a connector housing shielded by incorporating polymer blends according to the present invention.

DETAILED DESCRIPTION

Figure 1:
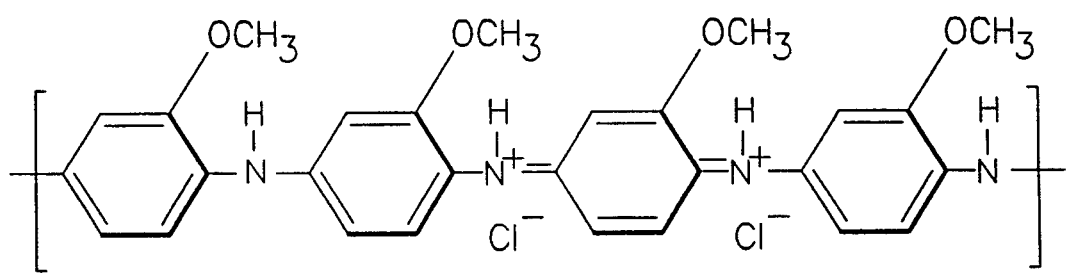
FIG. 1 is an illustration of an oxidized form of polyanisidine.
Figure 2:
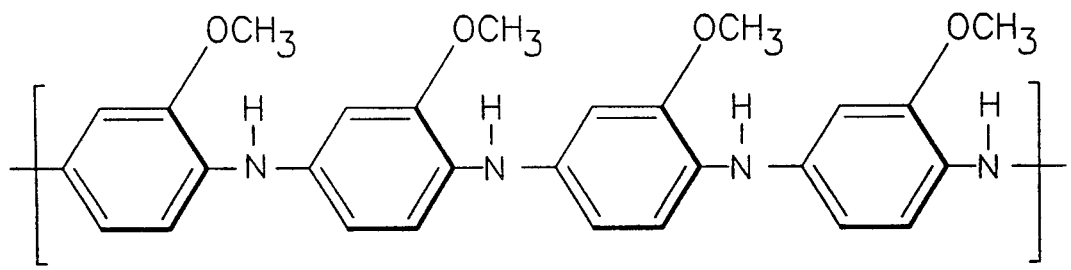
FIG. 2 is an illustration of a reduced form of polyanisidine.

Polyanisidine (hereinafter referred to as PANIS) is a relatively new electrically conductive polymer that is generating much interest due to its combination of air stability, electrical conductivity, and solubility in organic solvents. This unique blend of properties has been heretofore unavailable in synthetic conductors. PANIS is synthesized by either chemical or electrochemical means. The polymer may exist in at least four unique states; acid or base, oxidized or reduced. Each state is a function of the level of oxidation and protonation, and each is characterized by a unique set of electrical and optical properties, solubility and air-stability. The states are easily convertible by simple chemical and electrical means. As presently best understood, the most conductive and stable form of PANIS is the 50% oxidized acid form illustrated in FIG. 1.

The 50% oxidized acid form of PANIS is a dark green crystalline polymer having a molecular weight of approximately 2200 and a conductivity of 13.0 s cm$^{-1}$ (siemens per centimeter). PANIS does not have a defined melting point and begins to degrade at approximately 450° C. The presence of the pendant orthomethoxy groups allow dissolution in various common solvents, such as N,N-dimethylformamide, trifluoroacetic acid, and N-methylpyrrolidinone.

The potential applications of PANIS are widely varied and span the range from the utilization of the polymer's electrical properties, (e.g. polymeric electrodes), to the optical properties of the polymer, (e.g. optical switching devices). The fabrication of such articles, however, requires that the polymer be processable utilizing the current state-of-the-art industrial technology. Although the solubility of PANIS facilitates certain wet processing techniques, the dry polymer remains quite intractable and possesses less than desirable physical properties.

Therefore, the present invention comprises polymerization processes for the production of PANIS; processes for blending PANIS with other polymers to obtain blends with the desirable electrical and physical properties; and particular applications including a polymeric electrode, and a shielded connector. The present invention also comprises the use of the conductive polymer, its application onto a conductive substrate and its use as an electro-optical device.

EXPERIMENTAL

SYNTHESIS OF PANIS BY OXIDATIVE POLYMERIZATION

The oxidized acid form of poly-o-methoxyaniline (polyanisidine, $C_{14}H_{13}O_2N_2Cl$) can be chemically prepared in air by reacting a cold solution (approximately 5° C.) of ammonium peroxydisulfate ($(NH_4)S_2O_8$): in hydrochloric acid (HCl) with a cold solution (approximately 5° C.) of o-anisidine in hydrochloric acid. The two solutions are allowed to react for at least one hour in an ice bath with constant stirring. The resulting polymer is filtered from the deep purple solution and vacuum dried, producing a dark emerald green crystalline powder which displays very low electrical resistance. Several synthesis techniques were developed and one is described below.

CHEMICAL SYNTHESIS OF PANIS

PANIS was polymerized chemically in air by the oxidative polymerization of o-anisidine by ammonium peroxydisulfate. A 21.60 g sample of o-anisidine (Aldrich) was dissolved in 1 M hydrochloric acid and cooled in an ice bath at 5° C. Ten grams of ammonium peroxydisulfate (Fisher) were dissolved in 200 mL of 1 M hydrochloric acid at 5° C. and placed in a separatory funnel above the o-anisidine solution to facilitate dropwise addition. The ammonium peroxydisulfate solution was slowly introduced into the o-anisidine solution over an approximately 10 minute period with constant stirring. After 1 hour of stirring at 5° C., the solid PANIS was filtered out, rinsed with 1 M hydrochloric acid, rinsed with distilled water, and dried under dynamic vacuum at 60° C. A 10.2 g sample of dark, emerald green crystalline PANIS was produced (47.2% yield). The PANIS powder exhibited a low resistance of less than 5 ohms when checked with an ohmmeter.

ELECTROCHEMICAL SYNTHESIS OF PANIS

Polyanisidine can be polymerized from o-anisidine electrochemically. One gram of o-anisidine was dissolved in approximately 100 mL of 1 M hydrochloric acid and placed in a 250 mL beaker. Two approximately 4 cm$^2$ ITO glass electrodes were partially submerged in the solution to create an electrochemical cell and the solution was deoxygenated with argon. The cell was connected to a power supply (EPSCO model 612T) and 3 mA of current was passed through the cell for eighty minutes, depositing a dark green film on the anode. The electrode was removed, washed in 1 M hydrochloric acid, washed in distilled water, and allowed to dry. Using the measured number of coulombs passed through the cell, the calculated weight of PANIS produced Was 9.25 mg. The measured conductivity of the PANIS was 13 5/cm.

TESTING METHODS

UV-Visible Spectra

Each form of PANIS has a unique color. In particular, the oxidized acid form is dark green and shows a strong absorption peak in the range from 825 nm to 875 nm. Therefore, UV-visible spectra can be used to indicate the presence of the proper form of PANIS. UV-visible spectra were recorded on a Hitachi Model U-2000 spectrophotometer scanning between 320 nm and 1100 nm which clearly show the absorption peaks of the material.

Electrical Resistance

Two-point resistance values were obtained on a FLUKE digital ohmmeter. Two methods were developed to measure resistance through the thickness of a sample. In the first method (hereafter referred to as Method One), Indium-Tin-Oxide (ITO) conductive glass electrodes were coated with various polymer blends. Intimate contact with the polymer surface was achieved using a drop of mercury contained in a small O-ring as one point of contact and the ITO surface as the other point of contact. This method is only useful for well formed films having no voids or pinholes. In the second method shown in FIG. 9 (hereafter referred to as Method Two), the film sample 20 was placed on gold foil 21. The circuit was formed by placing one gold plated probe 22 (diameter 1/16 inch) in contact with the top surface of the sample 20 with a 100 g weight 23 used to standardize contact pressure while resting another probe 24 on the gold foil. This test method also included the ohmmeter 25 as well as the surface 26 upon which the gold foil 21 and the sample 20 rest. Very small samples were easily measured with Method Two.

In Method Two the following equation was used to calculate the conductivity:

$$\sigma = 4t/\pi d^2 R \quad \text{Eq. 1}$$

where $\sigma$ = conductivity in (ohm-cm)$^{-1}$ or S/cm
d = diameter of the sample probe contact area in cm
R = measured resistance in ohms Resistance along the plane of the film was measured by using two small pools of mercury contained in small O-rings about 1.25 cm apart. Ohmmeter leads were inserted in the mercury pools and the measured resistance was recorded.

Film Appearance

A Nikon stereomicroscope fitted with a polaroid camera was used to produce photomicrographs at magnifications of 100X, 200X, and 400X. At the relatively low magnification of 100X, the dark brown or green films appeared to have a fairly uniform mottled appearance. At magnifications of 200X and 400X, regions of clear host polymer were seen, evenly dispersed with fibrils of the darker polyanisidine.

POLYMER BLENDS

The term "polymer blend" as used here refers to the physical mixing of two polymers in an attempt to utilize the unique properties of each polymer in the resulting mixture. Although there are various approaches to such combinations, the work discussed here deals exclusively with processes where polymer solutions are mixed.

In this embodiment, the invention comprises a blend of an intrinsically conductive polymer and a nonconductive polymer; the conductive polymer being soluble in its conductive state in organic solvents in which the nonconductive polymer is also soluble; and the nonconductive polymer and the conductive polymer being present in said blend in a proportion sufficient to produce a conductivity of at least about $1.0 \times 10^{-7}$ siemens/cm in the conductive polymer blend.

In a preferred embodiment, the nonconductive polymer and the conductive polymer are present in the blend in a proportion sufficient to produce a conductivity of at least about $1.3 \times 10^{-2}$ siemens/cm in the resulting blend. Such a preferred embodiment will generally comprise between about 5 and 90 percent by weight polyanisidine, and in the most preferred embodiments will comprise between about 25 and 75 percent by weight polyanisidine.

PANIS Film

As previously reported, polyanisidine can be dissolved in N,N-dimethylformamide (DMF). Due to lack of total dissolution, a 10% (w/v) mixture of PANIS in N,N-dimethylformamide was further diluted to 1% (w/v). The resulting solution was dark brown in color. The solution was poured onto a watch glass and dried under an infrared heat lamp. Upon solvent evaporation in air, under the infrared lamp, a dark brown powder was produced. The powder exhibited poor film properties, was brittle, and would not form a free-standing film. A 10% (w/v) solution of PANIS in trifluoroacetic acid was prepared. The dark, emerald green solution was swabbed onto a clear glass slide and allowed to air dry. The resulting film was dark green, well adhered to the glass surface (impossible to remove intact), smooth, well formed, and had no visible pinholes or voids.

PANIS/Polystyrene Film

A ten percent (w/w) solution of polystyrene in N,N-dimethylformamide was prepared. Two grams of the solution were mixed with 2 grams of one-half percent PANIS in N,N-dimethylformamide (w/w). Such mixture yields a dried film consisting of approximately 5% PANIS. The resulting mixture was applied by spin casting onto a glass microscope slide and then drying under an infrared heat lamp. This procedure yielded a strong film that could be readily peeled from the glass substrate. The polyanisidine, however, did not appear to be well dissolved, as the film had a granular, particulate appearance.

A characteristic absorption peak at 841 nm in the UV-visible spectrum indicated that the conductive form of PANIS was present in the polystyrene; however, these results could not be consistently duplicated. The two-probe surface resistance tests gave infinite resistance. An alternate solvent (trichloroethylene) for the polystyrene solution was used in an attempt to achieve better film formation. Films were formed by dissolving expanded polystyrene in trichloroethylene and then adding various amounts of a solution of PANIS dissolved in N,N-dimethylformamide. Films containing over 90% PANIS were formed, none of which showed any conductivity when tested for electrical resistance. It is expected, however, that certain techniques discussed later herein this work may be applied to yield PANIS/polystyrene mixtures with increased conductivities. These techniques are discussed in the following sections.

PANIS/Poly(trimethyl hexamethylene terephthalamide)

Films of various concentrations of PANIS in Poly(trimethyl hexamethylene terephthalamide) a polyamide, also known as Nylon 6T, were prepared by dissolving both polymers in triflouroacetic acid ($CF_3COOH$) and spreading the solutions onto glass slides and ITO electrodes by passing them under a stationary blade to achieve a wet film thickness of approximately 0.2 mm. Films were also prepared using N-methylpyrrolidinone as the solvent. Surface resistance and resistance through the thickness of the film (Method Two) were measured. The results are shown in Tables 1, 2 and 3.

TABLE 1

Polymer Blends of Polyansidine and Poly(Trimethyl hexamethylene Terephthalamide)

| SAMPLE | % PANIS (a) | % SOLIDS (b) | SOLVENT | RINSE (c) | FILM (d) |
|---|---|---|---|---|---|
| 1. | 0 | 17 | TFA (e) | M | EXCELLENT |
| 2. | 25 | 17 | NMP (f) | W | GOOD |
| 3. | 25 | 17 | NMP | M | GOOD |
| 4. | 25 | 17 | NMP | N | GOOD |
| 5. | 25 | 20 | TFA | W | EXCELLENT |

TABLE 1-continued

Polymer Blends of Polyansidine and Poly(Trimethyl hexamethylene Terephthalamide)

| SAMPLE | % PANIS (a) | % SOLIDS (b) | SOLVENT | RINSE (c) | FILM (d) |
|---|---|---|---|---|---|
| 6. | 25 | 20 | TFA | M | EXCELLENT |
| 7. | 25 | 20 | TFA | N | EXCELLENT |
| 8. | 50 | 17 | NMP | W | GOOD |
| 9. | 50 | 17 | NMP | M | POOR |
| 10. | 50 | 17 | NMP | N | POOR |
| 11. | 50 | 20 | TFA | W | FAIR |
| 12. | 50 | 20 | TFA | M | FAIR |
| 13. | 75 | 17 | NMP | W | POOR |
| 14. | 75 | 17 | NMP | M | POOR |
| 15. | 75 | 17 | NMP | N | POOR |
| 16. | 75 | 17 | TFA | W | FAIR |
| 17. | 75 | 17 | TFA | M | FAIR |
| 18. | 75 | 17 | TFA | N | FAIR |
| 19. | 90 | 11 | TFA | W | POOR |
| 20. | 90 | 11 | TFA | M | FAIR |
| 21. | 90 | 11 | TFA | N | POOR |
| 22. | 100 | 17 | TFA | W | POOR |

(a) Percent PANIS in dry film.
(b) Percent Solids in solution.
(c) Rinse Types, M = Methanol, W = Water, N = None
(d) Film Physical characteristics.
(e) Trifluoroacetic acid.
(f) N-methylpyrrolidinone.

TABLE 2

Effect of rinse on film conductivity for several PANIS/polyamide blends

| SAMPLE | % PANIS (a) | SOLVENT | RINSE (b) | OHM (c) | S (d) | CONDUCTIVITY (d) |
|---|---|---|---|---|---|---|
| 2. | 25 | NMP (e) | W | 1.2M | 1.5E-4 | 1.194E-5 |
| 3. | 25 | NMP | M | 1.0M | 2.5E-4 | 1.990E-5 |
| 4. | 25 | NMP | N | 1.2M | 2.5E-4 | 1.990E-5 |
| 5. | 25 | TFA (f) | W | 2.0M | 1.0E-4 | 5.093E-6 |
| 6. | 25 | TFA | M | 3.0M | 3.2E-4 | 1.725E-6 |
| 7. | 25 | TFA | N | 4.1M | 5.0E-4 | 3.786E-6 |
| 11. | 50 | TFA | W | 100K | 4.0E-3 | 5.174E-5 |
| 12. | 50 | TFA | M | 120K | 1.7E-3 | 8.488E-5 |
| 13. | 75 | NMP | N | 120K | 1.9E-4 | 9.486E-6 |
| 17. | 75 | TFA | W | 10K | 1.3E-2 | 1.552E-3 |
| 18. | 75 | TFA | M | 10K | 1.3E-2 | 1.552E-3 |
| 19. | 75 | TFA | N | 10K | 1.3E-2 | 1.552E-3 |

(a) Percent PANIS in dry film.
(b) Rinse Types: M = Methanol; W = Water; N = None.
(c) Electrical Resistance measured through the Thickness of the sample using Method two calculated using equation 1.
(d) Conductivity in siemens/cm ((ohm-cm)$^{-1}$) calculated using Equation 1. Median values were used whenever there were several samples measured.
(e) N-methylpyrrolidinone.
(f) Trifluoroacetic acid.

TABLE 3

Percent PANIS versus Conductivity for Several PANIS/Nylon Blends

| SAMPLE | SOLVENT/ RINSE | % PANIS (a) | CONDUCTIVITY (b) |
|---|---|---|---|
| 2. | NMP (c)/water | 25 | 0.00001194 |
| 8. | NMP/water | 50 | 0.00001698 |
| 5. | TFA (d)/water | 25 | 0.000005093 |
| 11. | TFA/water | 50 | 0.00005174 |
| 17. | TFA/water | 75 | 0.001552 |
| 6. | TFA/methanol | 25 | 0.000002725 |
| 12. | TFA/methanol | 50 | 0.00008488 |
| 18. | TFA/methanol | 75 | 0.001552 |
| 21. | TFA/methanol | 90 | 0.0005093 |
| 1. | TFA/methanol | 0 | |
| 22. | TFA/methanol | 100 | 0.06 (e) |

(a) Percent PANIS in dry film.
(b) Siemens/cm (ohm-cm)$^{-1}$ calculated using equation 1.
(c) N-methylpyrrolidinone.
(d) Trifluoroacetic acid.
(e) 13 S/cm when done by four-point probe technique.

Conductivity of Blended Films

Most of the film samples had conductivities (or resistances) of magnitudes not easily measured using a four probe method. For this reason, Method Two was found to give what are believed to be the most consistent and, it is felt, reliable readings. A comparison between Method Two and four probe methods can be seen by a comparison of the measured conductivity of pure PANIS. When PANIS was dissolved in TFA and cast into a film, Method Two gave a conductivity of 0.06 S/cm. Measurement of the same sample using a four probe technique gave a conductivity of 13 S/cm, identical to that found for pressed powder samples of polyansidine.

PANIS/Polyacrylonitrile Film

In response to the characteristics of the PANIS/polystyrene blends, polyacrylonitrile (PAN) was selected as a replacement for the polystyrene. The following description of this work is organized into three segments. The first two segments, Mastication and Solvents, describe certain preparations made to facilitate better processing and enhanced physical, electrical, and optical properties of the final article. The final sections, Film and Fiber, describe the actual methods of fabrication.

POLYMER BLEND PREPARATION TECHNIQUES

In another embodiment, the invention comprises a method of forming a conductive polymer blend. The method comprises solvating a mixture of polyanisidine and polyacrylonitrile in N,N-dimethylformamide, and extracting a substantial amount of the N,N-dimethylformamide solvent from the polymer blend mixture using a solvent removal agent in which the solvent is more soluble than the mixture. In particular, the step of extracting the mixture preferably comprises removing the solvent by rapidly immersing the solvated mixture in a solvent removal agent. In a most preferred embodiment, the step of removing the solvent comprises immersing the solvated mixture in a solvent removal agent selected from the group consisting of water, and methanol.

As for proportions present in the mixture, the method preferably comprises solvating a mixture of between about 5 and 90 percent by weight polyanisidine, and most preferably a mixture of between about 25 and 75 percent by weight polyanisidine.

Mastication (Grinding)

Early results with PAN were much the same as with polystyrene, as evidenced by highly granular films of moderate flexibility. In order to reduce the particle size and improve on the consistency of the powder, equal portions by weight of PANIS and PAN were placed into a small plastic rotary tumbler with two one-half inch steel ball bearings and approximately one tablespoon of irregular steel shot. Ten to twelve grams of powder were masticated for approximately thirty minutes, resulting in a very uniform powder. The powder was then separated from the shot using a fine mesh screen (approximately 42 mesh or 0.350 mm opening. The 1:1 (PANIS/PAN) powder had a very uniform texture not unlike sifted flour and a medium gray color. The free flowing powder displayed infinite electrical resistance. A pressed pellet of the same mixture, however, showed a significant reduction in resistance.

Solvents

A uniformly solvated mixture is necessary for adequate processability and proper dispersion of the solids in the final product. Approximately 0.005 g of the previously masticated 50/50 by weight PANIS/PAN mixture were weighed into each of several numbered test tubes and then one milliliter of a selected solvent was added to each tube and the mixture was observed for solvation. The results are shown in Table 4.

TABLE 4

Solubility of 1:1 PANIS:Polyacrylonitrile Blends

| SOLVENT | OBSERVATION |
|---|---|
| N,N-dimethylformamide | Fluid, dark green solution<br>Few small undissolved particles<br>Required heating for best results |
| Sulfuric Acid, 96% | Viscous, dark blue-green solution<br>Numerous undissolved particles |
| Acetic Acid, conc. | Fluid red-brown solution<br>Numerous undissolved particles |
| Ammonium Hydroxide, conc. | No visible signs of solvation |
| Ethylene Glycol | Viscous, dark green solution<br>Few undissolved particles<br>Similar appearance as DMF solution |
| Methyl Isobutyl Ketone | Dark red-brown solution<br>Seemed will dissolved<br>Particle formation upon evaporation |
| Methyl Alcohol | Dark brown solution<br>Numerous undissolved particles |
| Acetone | No visible signs of solvation |
| Trifluoroacetic acid | Dark green solution<br>Elastic solid upon evaporation |
| Acetonitrile | Rapid solvation and evaporation of solvent. No film formation upon evaporation |
| N,N-dimethylacetamide | Dark black solution<br>Numerous undissolved particles |

Spatula Rubout

Films containing various concentrations of PANIS were prepared using a technique whereby the polymers and solvents were placed onto a glass dish and vigorously mixed with a stainless steel laboratory spatula utilizing a circular motion while holding the spatula flat against the glass dish. This type of mixing was observed to give greater dissolution, particle size reduction and particle wetting. Solvent can be added during the process to obtain the desired viscosity (excess solvent, however, may promote excessive film shrinkage and poor adhesion to the substrate). The liquid polymer/solvent mixture can be subsequently poured onto a smooth surface where film formation would occur upon solvent evaporation. This same liquid mixture can also be spin cast to form a film (see Spin Casting).

A film containing approximately 85% (w/w) PANIS was prepared from 0.05 g PANIS and 0.10 g of a 9% by weight solution of polyacrylonitrile in N,N-dimethylformamide and mixed as explained above. No additional N,N-dimethylformamide was required. A dark purple solution was produced. The polymer/solvent mixture was then spread with a spatula onto glass slides and ITO glass electrodes. Films were allowed to form by solvent evaporation in air and under infrared radiation. A dull, dark green (almost black) film was formed. The film was well adhered to the glass. A sample of the film was removed from the glass and was free standing, flexible (although more brittle than pure polyacrylonitrile films), and free from any visible pinholes. The undersurface of the film appeared quite smooth and shiny.

Additional concentrations (92%, 50% and 25%) were similarly prepared. The 92% mixture lacked sufficient cohesion for film formation, but the lower concentrations produced good films with improved physical properties.

Spin Casting

A small laboratory centrifuge was modified to rotate glass slides and ITO glass plates at various speeds as drops of solvated polymers were dropped on the spin axis. This technique was used to make thin films. The films were of relatively poor quality as some were slightly granular (depending on solvent) and none were conductive.

Solvent Removal

The most effective method found for forming a conductive film or fiber was by solvating the PANIS/PAN mixture in N,N-dimethylformamide. The solvation was immediately followed by rapid solvent removal of the polymer by immersion in methanol or water. The solvent removal agent quickly removes the N,N-dimethylformamide solvent, forming a dark green, tar-like gel that can easily be spread into a film or formed as a fiber.

Film

A film containing 50% PANIS was produced as follows: 0.10 g of a pulverized 1:1 (w/w) mixture of PANIS and polyacrylonitrile was dissolved in 0.5 mL N,N-dimethylformamide. To this solution, 0.5 mL of methanol was added and mixed with the immediate formation of a dark green tar-like gel. A portion of this gel was removed and spread onto a plain glass slide where it was allowed to air dry. Additional N,N-dimethylformamide was added to the remaining portion of the gel-like blend until a free-flowing liquid was formed. A sample was poured onto a glass slide and allowed to air dry. The resulting films were dull, dark green and well adhered to the glass. A sample of the film was removed with a knife. The films were well formed, free standing, and flexible. When viewed with a stereo microscope, the surface appeared to be a random maze of dark green PANIS and pale green polyacrylonitrile areas, was quite irregular, and contained frequent nodules. The surface of the film in contact with the glass, however, was quite smooth and shiny.

The films were subjected to the two probe surface resistance test. Both the top and bottom surfaces showed significant reduction in resistance from the parent polyacrylonitrile polymer (going from an insulator to 1 Megaohm resistance for a 0.1 mm thick film). The films also exhibited an immediate color change (dark green to blue) when subjected to 1 M ammonium hydroxide, indicating a color change from the green acid conducting state to the blue basic insulating state.

Subsequently, films containing various concentrations of PANIS and PAN were prepared. Proper amounts of the polymers were weighed, mixed, and dissolved in N,N-dimethylformamide. Uniform films were prepared by applying a small amount of the solution to the end of a clean glass slide and passing the slide under a stationary blade (approximate wet film thickness 0.2 mm). The coated slide was immediately dipped in a bath of cold distilled water or methanol and then allowed to air dry. Surface resistance and resistance through the thickness of the film (Method Two) were measured. The results are shown in Table 5. Surface resistance measurements gave very high readings, 15 Megaohms or greater, and are not shown in the table.

rod, and its resistance dropped to about 1 megohm across a 2.5 cm sample length.

APPLICATIONS

Optical Switching Device

An optical switch as described herein is a device which changes optical properties upon application of an electrical potential, in this case from green (oxidized PANIS) to yellow (reduced PANIS).

In this embodiment, the optical switching device comprises first and second substantially transparent electrodes adjacent to one another with an electrically and ionically conductive medium therebetween, and a coating on one surface of the first electrode and formed of an intrinsically conductive polymer that is in electrical contact with the first electrode and with the electrically conductive medium. The conductive polymer has respective oxidized and reduced forms that have different transparencies to varying frequencies of light so that a potential difference applied across the electrodes will

TABLE 5

| | | | PANIS/Polyacrylonitrile Blends | | | |
|---|---|---|---|---|---|---|
| % PANIS (a) | % SOLIDS (b) | RINSE (c) | FILM (d) | THICK (e) | OHM (f) | CONDUCTIVITY |
| 25 | 17 | W | FAIR | 0.050 | 10M | 2.03-5 |
| 25 | 17 | M | POOR | — | — | — |
| 25 | 17 | N | NONE | — | — | — |
| 50 | 17 | W | GOOD | (h) | (h) | (h) |
| 50 | 17 | M | FAIR | 0.075 | 1M | 1.3E-4 |
| 50 | 17 | N | FAIR | 0.075 | 1M | 1.3E-4 |
| 75 | 17 | W | NONE | — | — | — |
| 75 | 17 | M | NONE | — | — | — |
| 75 | 17 | N | NONE | — | — | — |

(a) Percent PANIS.
(b) Percent Solids.
(c) Rinse Types: M = Methanol; W = Water; N = None.
(d) Film Physical Characteristics.
(e) Film Thickness in cm.
(f) Electrical Resistance Through the Thickness of the Sample in ohms.
(g) Conductivity in S/cm or (ohm-cm)$^{-1}$
— No Measurement Due to Poor Film Formation.
(h) Not measured.

Fiber

In yet another embodiment, the invention comprises a method of forming fibers from a blend of an intrinsically conductive polymer and a nonconductive polymer by forming a blend solution of an intrinsically conductive polymer and a nonconductive polymer in a solvent in which the intrinsically conductive polymer is soluble in its conductive state and in which the nonconductive polymer is also soluble, and then extruding the solvated blend solution through a small diameter orifice into a solvent removal agent. In a preferred embodiment, the method further comprises the steps of stretching the resulting extrudate to increase its tensile strength and conductivity, and the step of removing residual solvent from the extrudate.

In a typical process, fibers can be easily extruded from the 1:1 PANIS/PAN solution in N,N-dimethylformamide by using methanol as a solvent removal agent. One gram of the PANIS/PAN mixture was dissolved in 10 mL of N,N-dimethylformamide and drawn into a syringe. The tip of the syringe was immersed in a beaker of methanol and a thin thread was slowly extruded from the syringe. The polymer immediately congealed into a mushy, dark green flexible fiber. The fibers were washed in distilled water and either air dried or dried under dynamic vacuum to remove all traces of the solvent. While still wet, a sample of the fiber was drawn to approximately twice its original length. After drying, the texture of the fiber changed to that of a rigid generate a current flow through the conductive polymer that respectively oxidizes or reduces the polymer to thereby change its light transmission characteristics.

In a preferred embodiment, the first and second electrodes are in substantially parallel relationship with the conductive medium and the conductive polymer therebetween, and the conductive polymer comprises polyanisidine. In this embodiment, each substantially transparent electrode comprises a glass substrate coated with an indium-tin-oxide coating, and the overall device will change its light transmission characteristics in less than one second upon the application of 1.5 volts potential.

Such a device is illustrated in FIGS. 7 and 8 and broadly designated at 30. The optical device 30 utilizes two, approximately 4 c$^2$, single conductive surface ITO glass electrodes 31 and 32, one O-ring 33, and epoxy glue (not shown). The O-ring 33 was notched to form an opening 36 therein and glued to the respective conductive surface 34 and 35 of each electrode 31 and 32 as shown in FIGS. 7 and 8. Appropriate electrical connections were made through the wires illustrated schematically at 37 and 38.

In this regard, the invention also comprises the method of making the optical switching device. The method includes the steps of adding o-anisidine and an acid to a resevoir between two respective electrodes, and applying a potential difference across the electrodes of an amount and for a time sufficient to polymerize the o-anisidine to polyanisidine. In the preferred embodiment, the step of adding o-anisidine and an acid to the resevoir between the electrodes comprises adding o-anisidine and an acid to a resevoir between two substantially transparent electrodes which are most preferably glass electrodes coated with an indium-tin-oxide coating. Furthermore, the step of adding an acid preferably comprises adding an aqueous solution of hydrochloric acid.

More specifically, the reservoir inside the O-ring 33 was subsequently filled with 1 M hydrochloric acid. O-anisidine was added, electrochemically polymerized, and simultaneously deposited onto a single electrode surface (see Electrochemical Synthesis of PANIS). The remaining solution was removed and the PANIS film was allowed to dry in a vacuum desiccator. Upon removal of the device from the desiccator, the light green film appeared to be continuous and pore-free but somewhat irregular, with random dark green specks. The reservoir was again filled with 1 M hydrochloric acid and upon application of $+1$ V the film changed from green to yellow within 3 to 6 seconds, with the change first being evident in the areas of dark green. A potential of $-1$ V changed the film from yellow to green within a similar time span. It was subsequently discovered that the voltage supplied from a common 1.5 V dry cell battery would switch the color in less than one second.

Inert Conductive Polymer-Blend Coated Electrodes

In another embodiment, the invention comprises an inert electrode, i.e. an operative electrode with a chemically inert surface, that is formed using the conductive polymer blends of the present invention. As is known to those familiar with electrode chemistry, in some instances, the dissolution of electrode materials provides a useful purpose. Examples include battery usage or electroplating applications where material from one electrode is transferred to the other electrode through ion transport in solution and respective oxidation and reduction reactions at the anode and cathode.

For other applications, however, the use of an electrode which is chemically inert to the solution environment is desirable, preferred, or even necessary. Such applications include precious metal electroplating in which the solution concentration is depleted to plate out the precious metal; biological sensors; potential pickups; chemical species detection; and solution pH measurement, among others.

When electrodes are used for chemical species detection or biological applications, corrosive attack of the electrode is undesirable and leads to loss of functionality of the electrode. As a result noble metals such as gold or platinum are often used for such applications because of their stability and consequent resistance to chemical attack. Noble metals, however, tend to be very expensive to obtain and use. Therefore, the invention provides a method and associated product of an inert electrode surface without using noble metals and therefore providing a substantial technical advantage.

In this embodiment, the invention comprises a conductive electrode substrate and a chemically inert conductive coating in physical and conductive contact with the electrode substrate. Preferred electrode substrates include platinum and ITO coated glass. The coating is formed of a blend of an intrinsically conductive polymer and a nonconductive polymer in which the conductive polymer is soluble in its conductive state in organic solvents in which the nonconductive polymer is also soluble. The amount of the nonconductive polymer in the blend is sufficient to prevent the conductive polymer from undergoing oxidation-reduction or other chemical reaction during the application of voltage and to prevent the conductive polymer from the degrading action of irreversible over-oxidation at applied voltages that are greater than the applied voltages at which the conductive polymer would be irreversibly over-oxidized if the conductive polymer were in substantially pure form.

In the preferred embodiments, the conductive polymer comprises polyanisidine, and the blend comprises a blend extracted from a solution in which polyanisidine is soluble in its conductive state in a solvent in which the nonconductive polymer is also soluble. Preferably, the nonconductive polymer is selected from the group consisting of polystyrene, polyacrylonitrile, polyethylene oxide, poly(trimethyl hexamethylene terephthalamide), polyamide, polyester, acrylic, and polycarbonate polymers.

Additionally, the conductive coating preferably comprises a cast film, in which the conductive polymer comprises between about 5 and 90 percent by weight of the blend, and most preferably between about 25 and 75 percent by weight of the blend.

Expressed alternatively, the electrode of the present invention comprises a conductive electrode substrate, and a chemically inert conductive coating in physical and conductive contact with the electrode substrate that is formed of a blend of polyanisidine and polyacrylonitrile and that has a conductivity of at least about $1.0 \times 10^{-7}$ siemens/cm.

To produce the electrode, a 0.05 g sample of PANIS was added to 0.1 g of a 9% by weight solution of polyacrylonitrile in N,N-dimethylformamide (85% by weight PANIS, dry). This solution was coated onto the conductive surface of an ITO glass electrode and allowed to air dry. A dull, dark green (almost black), opaque film was produced. The film was well adhered to the surface of the electrode and appeared pinhole free.

Figure 6:
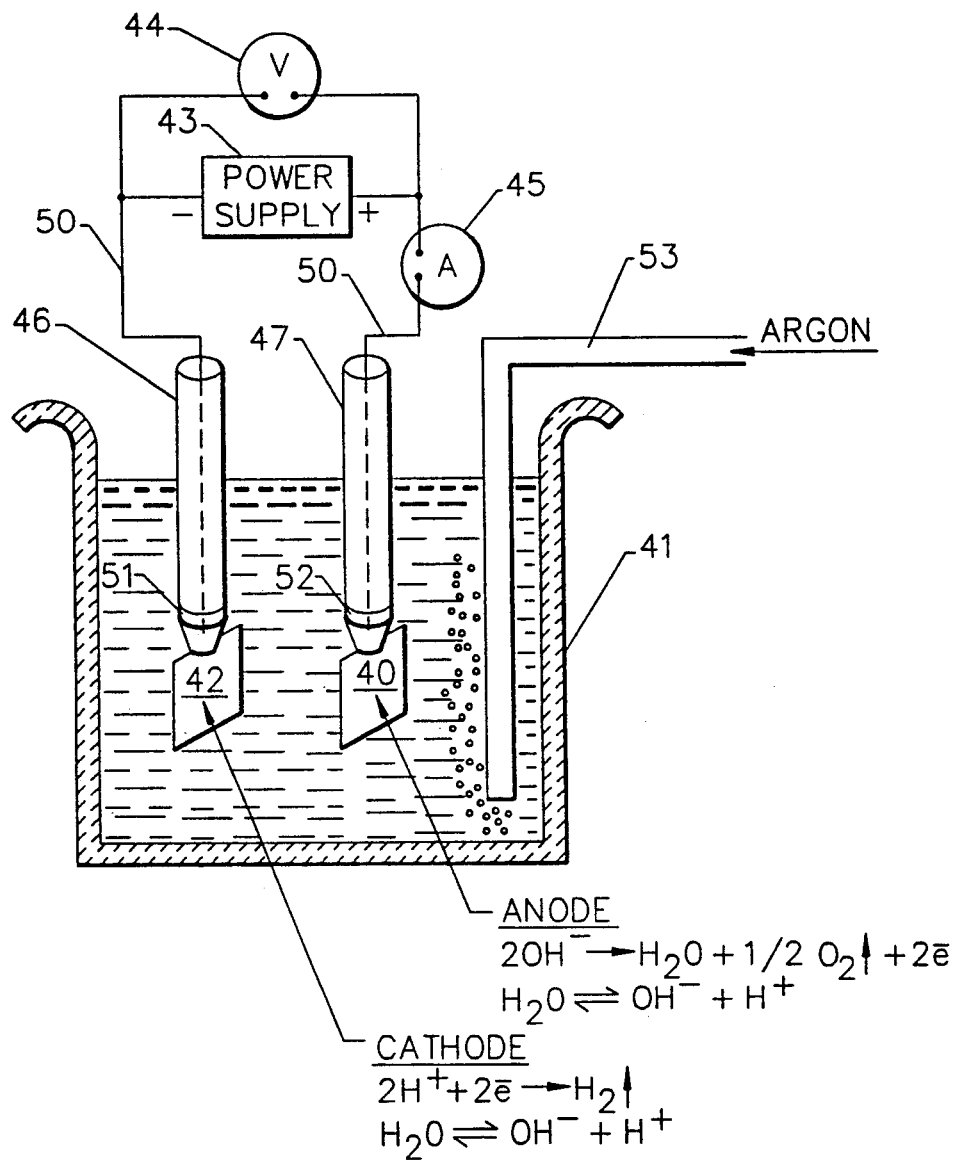
FIG. 6 is a schematic diagram of a cell in which the potentials were measured.

FIG. 6 illustrates an appropriate test cell. The electrode 40 was placed in a beaker 41 containing 1 M hydrochloric acid and a platinum electrode 42. The cell was attached to a DC power supply 43 (EPSCO model 612T). A potential of 1.8 V as measured on voltmeter 44 with 1 mA of current as measured on ammeter 45 was established and the cell was left for 3 hours upon which time the presence of hydrogen gas bubbles were observed on the platinum electrode and oxygen gas bubbles were observed on the polymer electrode.

FIG. 6 also illustrates that the test cell includes glass tubes 46 and 47 to protect the wiring so that helps make up the circuit, plugs 51 and 52 preferably formed of silicone rubber sealant, and glass supply tube 53 for supplying argon gas to the cell to maintain an inert atmosphere over the electrolyte solution.

In this regard, the invention also comprises a method of measuring electrical potential as well as an electrochemical cell. The method is one of measuring potential difference in electrolytic cells while avoiding chemical or electrochemical reactions between the electrodes and the electrolytes therein. It comprises applying a potential difference across a pair of electrodes wherein at least one of the electrodes comprises a conductive substrate coated with a chemically inert conductive polymeric blend of an intrinsically conductive polymer and a nonconductive polymer. The amount of the nonconductive polymer in the blend is sufficient to prevent the conductive polymer from undergoing oxidation-reduction or other chemical reaction during the application of voltage and to prevent the conductive polymer from the degrading action of irreversible over-oxidation at applied voltages that are greater than the applied voltages at which the conductive polymer would be irreversibly over-oxidized if the conductive polymer were in substantially pure form. In the preferred embodiment, the conductive substrate is coated with a blend of polyanisidine and polyacrylonitrile in which polyanisidine is present in an amount of between about 5 and 90 percent by weight, and in the most preferred embodiment, between about 25 and 75 percent by weight.

As an electrochemical cell, the invention comprises a container, an electrolyte in the container, an anode in the electrolyte, a cathode in the electrolyte and in electrical connection with the anode other than through the electrolyte, a source of electrical potential between the anode and the cathode, and wherein at least one of the anode or the cathode comprises a conductive substrate coated with a chemically inert conductive polymeric blend of an intrinsically conductive polymer and a nonconductive polymer and wherein the amount of the nonconductive polymer in the blend is sufficient to prevent the conductive polymer from undergoing oxidation-reduction or other chemical reaction during the application of voltage and to prevent the conductive polymer from the degrading action of irreversible over-oxidation at applied voltages that are greater than the applied voltages at which the conductive polymer would be irreversibly over-oxidized if the conductive polymer were in substantially pure form.

Further studies examined the current-voltage behavior over a range of +4 V to −4 V and an electrical comparison was made to a similar cell constructed with two platinum electrodes. Although the oxidation of water occurred at a higher voltage with the polymer electrode (2.4 V) than with the platinum electrode (1.3 V), the otherwise similar behavior of the two cells demonstrated the inert nature of the polymer electrode. In addition, the polymer did not change color during this process.

Figure 3:
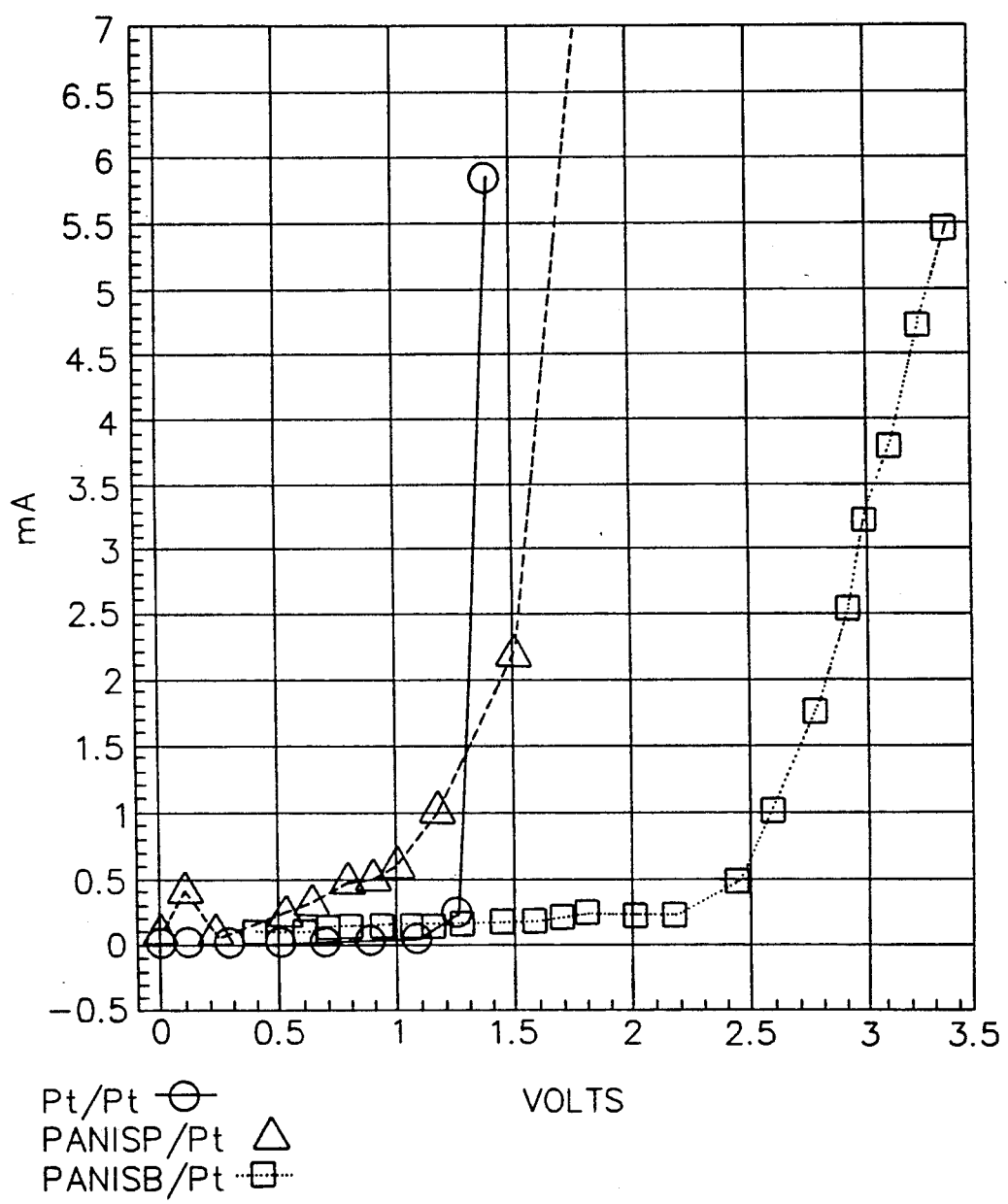
FIG. 3 is a current versus voltage plot for various electrodes measured against a standard platinum reference electrode including platinum, polyanisidine, and a blend of polyanisidine and polyacrylonitrile on platinum.
Figure 4:
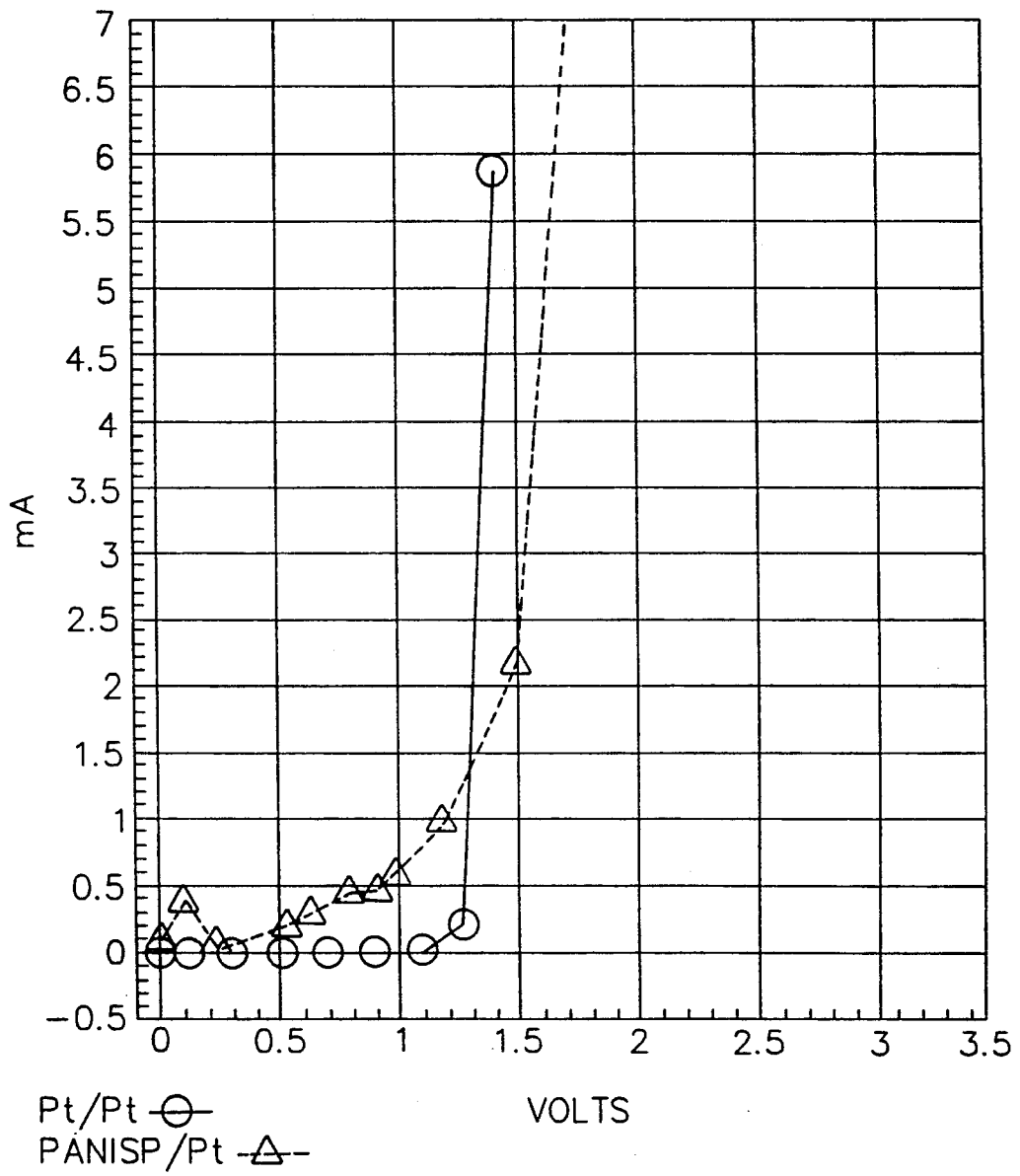
FIG. 4 is a breakout from FIG. 3 comparing the platinum electrode to the electrode formed of pure polyanisidine electrodeposited on platinum.
Figure 5:
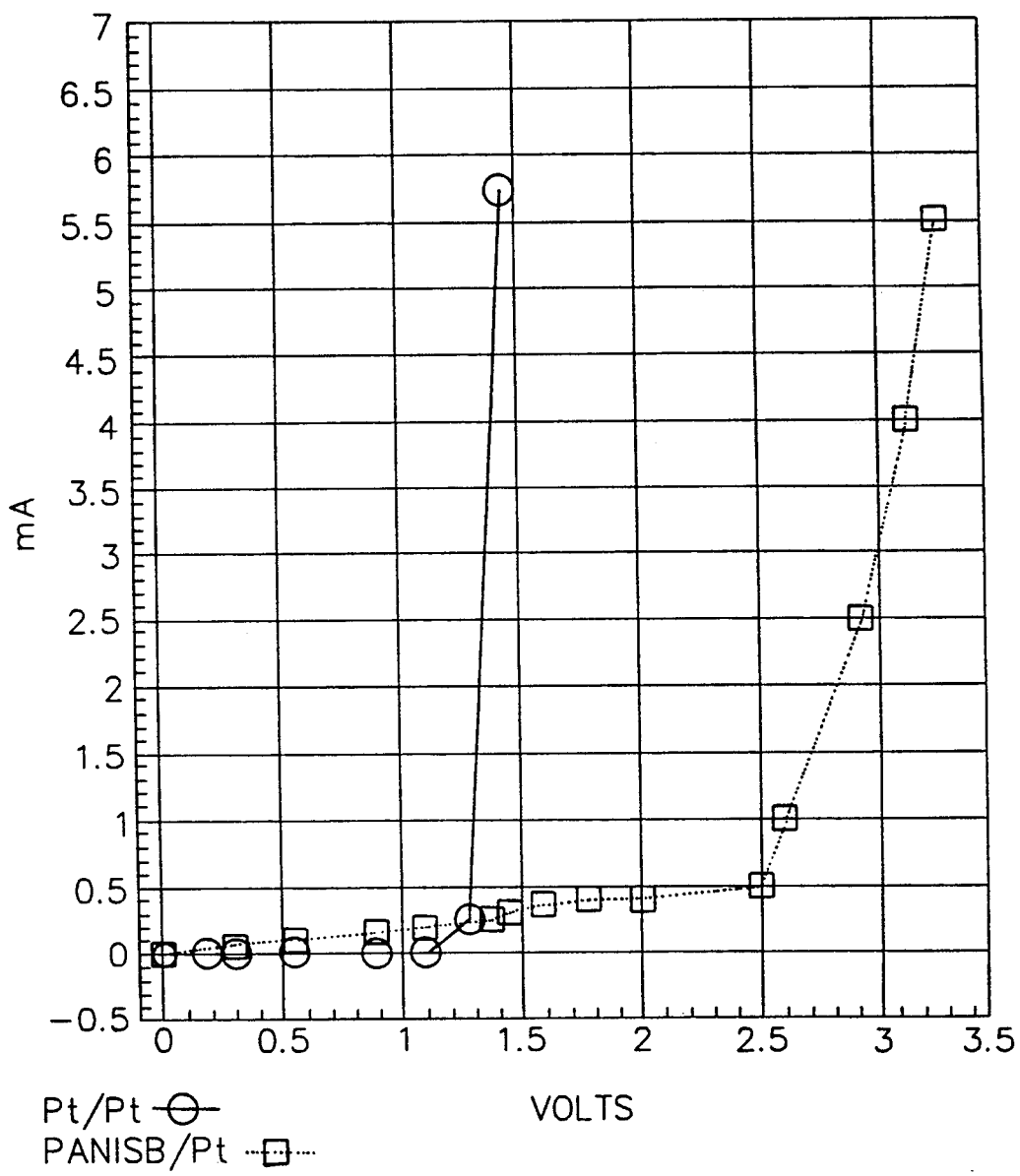
FIG. 5 is another breakout from FIG. 3 comparing the performance of the platinum electrode to an electrode formed of a blend of polyanisidine and polyacrylonitrile coated on platinum.

FIG. 3 illustrates a comparison of the current-voltage characteristics of similar electrochemical cells incorporating various anode surfaces. The cells all contain dilute hydrochloric acid and included platinum cathodes. The anodes compared were platinum ("Pt/Pt"), pure PANIS coated on platinum ("PANISP/PT"), and a PANIS blend coated on platinum ("PANISB/Pt"). FIGS. 4 and 5 are breakout versions of FIG. 3 that help illustrate the comparisons between All the cells had a 1 cm separation and were tested under argon (Ar) electrodes.

As observed during testing, using an apparatus as illustrated in FIG. 6, the pure PANIS anode electrode surface was reactive during its use in an electrochemical cell while the PANIS-blend polymer anode electrode surface remained inert and behaved similarly to a platinum anode.

Platinum Anode

FIGS. 3, 4, and 5 all illustrate the performance of the platinum anode. The current flow at zero volts was minimal until the point at which water dissociated and oxygen evolution took place, indicating the inertness of the platinum electrode to oxidation. The rapid increase in current at voltage levels beyond this point (about 1.3 volts), is responsible for a corresponding increase in the amount of oxygen produced.

PANIS Coated Platinum Anode (FIG. 4)

Starting at zero volts applied voltage with PANIS in its completely non-oxidized state (yellow color), the applied voltage was gradually increased. At rather low applied voltages, PANIS loses electrons, as demonstrated by the current flow, and oxidizes to its optimum conductive state (0 to about 0.25 volts) where it is approximately 50 percent oxidized (green color). As the voltage increases, PANIS continues to oxidize (as shown by the increased current flow) until oxygen evolution takes place. No attack of the PANIS by the evolved oxygen was observed during the course of the run. At an applied voltage of approximately 3.6 volts, PANIS becomes fully oxidized (blue color). At voltages about 3.6 volts, PANIS becomes over oxidized, loses conductivity, and passes the point at which it can be reversibly cycled by lowering the voltage.

PANIS-Blend Coated Platinum Anode (FIG. 5)

As previously indicated, the PANIS in the PANIS-blend was in its optimum conductive state (green color), and the applied voltage was increased, starting from zero volts. The absence of current flow indicates that the PANIS-blend electrode surface is similar to the platinum electrode surface and does not undergo oxidation. At the applied voltage where oxygen evolution takes place, the current flow increases rapidly, similar to the platinum electrode. The applied voltage level can be raised above the level where the PANIS electrode surface changed color and lost its capability to recover functionality with voltage reversal and no change in color of the PANIS-blend electrode surface and with no loss in its functionality. The voltage level can be cycled with no apparent loss in electrode surface functionality. Although FIG. 5 appears to indicate that the blend electrode operates at higher voltages than the platinum electrode, the voltage difference illustrated may be due to a voltage drop between the core of the electrode and the blended polymer surface, so that the potential difference in the solution may also be about 1.5 volts when oxygen evolves.

Electrical Shielding

The invention further comprises the use of electrically conductive polymer blends as an electrically conductive shielding surface for electrical interconnect systems as well as the method of preparing the shielding systems.

In some instances, metallic materials provide a useful electronic or electromagnetic interference shielding medium, such as in electrical connectors for signal lines, computer systems, electronic equipment cabinets, and electronic equipment housings.

Additionally, when electronic components are connected or wired to one another, the connectors for the wiring between them are likewise often favorably shielded. Applications for which shielded connectors are worthwhile include biological sensor applications, potential pickup, telecommunication systems, various test equipment, and most computer systems.

Typically, steel, nickel or gold plated metals are used for such shielding applications because of their general effectiveness. Metal shielding systems, however, are relatively expensive and susceptible to corrosion. Therefore, a shielded surface manufactured without the use of metals, would provide substantial advantages.

Accordingly, in this embodiment of the invention, the conductive polymer blends of the present invention are solvent cast onto an extruded or molded polymeric object that serves as an electrical interconnection housing. The conductive coating will shield the object from electromagnetic effects such as electrostatic discharge (ESD), electromagnetic interference (EMI) and radio frequency interference (RFI).

As particular advantages, the solvent cast conductive polymer blend coatings remain conductive and shielding even under conditions that would corrode metallic shielding materials and that would adversely affect the conduction properties of bulk conductive polymers.

In this embodiment, the shielded connector comprises a polymeric housing that in turn comprises a blend of an intrinsically conductive polymer and a nonconductive polymer wherein the amount of the conductive polymer in the blend is sufficient to shield electronic components within the housing from electromagnetic or electrostatic interference. In a preferred embodiment, the external surfaces of the polymeric housing are coated with the polymer blend, and the blend comprises polyanisidine and polyacrylonitrile and wherein the amount of polyanisidine in said blend is between about 5 and 90 percent by weight. In more preferred embodiments, the amount of polyanisidine in said blend is between about 25 and 75 percent by weight, and the blend has a conductivity of at least about $1.0 \times 10^{-7}$ siemens/cm.

In the preferred embodiment, a conductive polymer blend solution, as set forth earlier, can be applied to a connector housing by dipping, spraying, painting or other coating methods with a solvent removal accomplished as set forth earlier; i.e. air drying, heating at moderate temperatures, or contact with a solvent removal agent.

FIG. 10 illustrates a shielded connector according to the present invention broadly designated at 54. The connector includes a housing 55, coated With the conductive polymer blend 56, female receptacles 57 for wires, prongs or pins 60, junction hardware designated at 61, and output wires 62. By coating the housing 55 with an appropriate amount of the conductive polymer blends described herein, the junction between the contacts 60 and 62 can be effectively shielded from electromagnetic interference (EMI), but without resort to metals, and provided with the physical and chemical advantages offered by the polymer blends.

In summary, o-anisidine may be quickly and economically polymerized both chemically and electrochemically. Chemical preparation yields high quality, electrically conductive PANIS powder in reasonable quantities for which yields of over 50% appear easily obtainable. Although the electrochemical polymerization was not studied as thoroughly as the chemical polymerization, it is believed that the electrochemical processes can be developed that will produce good yields of high quality PANIS. Furthermore, it has been established that PANIS can be blended with other polymers to yield electrically conductive films and fibers. Although the blended polymers showed considerably higher electrical resistance than the pristine polyanisidine powder, the improved processability and physical properties more than compensate for the partial loss of conductivity. The precipitated films and fibers of PANIS/PAN and PANIS/Poly(trimethyl hexamethylene terephthalamide) mixtures exhibit the desirable properties of both the constituent polymers. The potential of PANIS technology has been further demonstrated by the construction of three devices: a switching device that will change color upon the application of positive and negative voltages, an inert polymer electrode, and an electromagnetically shielded connector.

What is claimed is:

1. An inert electrode comprising:
    an electrode substrate formed of an electrically conductive material; and
    a conductive coating polymer blend that is chemically inactive in oxidizing or reducing solution environments, said conductive coating polymer blend being in physical and conductive contact with said electrode substrate; and wherein
    said conductive coating polymer blend is formed of a homogeneous blend of polyanisidine and polyacrylonitrile in which said polyanisidine is present in an amount of between about 5 and 90 percent by weight; and wherein
    the amount of said polyacrylonitrile in said conductive coating polymer blend is sufficient to prevent said polyanisidine from undergoing oxidation-reduction during the application of voltage to said substrate and said conductive coating polymer blend; and wherein
    the amount of said polyacrylonitrile in said conductive coating polymer blend is sufficient to prevent said polyanisidine from the degrading action of irreversible over-oxidation when voltages are applied to said substrate and said conductive coating polymer blend that are greater than the applied voltages at which polyanisidine is irreversibly over-oxidized when polyanisidine is applied to a conductive substrate in substantially pure form.

2. An inert electrode according to claim 1 wherein said blend comprises a blend extracted from a solution in which said polyanisidine is soluble in its conductive state in a solvent in which said polyacrylonitrile is also soluble.

3. An electrode according to claim 1 wherein said conductive coating comprises a cast film.

4. An electrode according to claim 1 wherein said polyanisidine comprises between about 25 and 75 percent by weight of said blend.

5. An inert electrode according to claim 1 wherein said conductive substrate comprises platinum.

6. An inert electrode according to claim 1 wherein said conductive substrate comprises indium-tin-oxide coated glass.

7. An inert electrode according to claim 1 wherein said conductive coating polymer blend has a conductivity of at least about $1.0 \times 10^{-7}$ siemens/cm.

* * * * *